United States Patent [19]

Garst

[11] Patent Number: 5,559,078

[45] Date of Patent: Sep. 24, 1996

[54] AGRICULTURALLY ACTIVE COMPOSITION COMPRISING POLYHYDROXY ACID AMIDE ADJUVANT

[75] Inventor: Roger H. Garst, Cincinnati, Ohio

[73] Assignee: Henkel Corporation, Plymouth Meeting, Pa.

[21] Appl. No.: 348,554

[22] Filed: Dec. 1, 1994

[51] Int. Cl.$^6$ ........................................ A01N 25/30
[52] U.S. Cl. .................. 504/116; 424/405; 514/788; 514/943; 514/975; 71/DIG. 1
[58] Field of Search ............... 71/DIG. 1; 514/946, 514/943, 975, 89, 144, 531, 617, 646, 783; 504/234, 238, 327, 330; 424/405

[56] References Cited

U.S. PATENT DOCUMENTS

| | | | |
|---|---|---|---|
| H224 | 3/1987 | Malik et al. | 71/92 |
| H303 | 7/1987 | Malik et al. | 514/85 |
| 3,219,656 | 11/1965 | Boettner | 260/210 |
| 3,598,865 | 8/1971 | Lew | 260/210 R |
| 5,244,593 | 9/1993 | Roselle et al. | 252/99 |
| 5,288,431 | 2/1994 | Huber et al. | 252/548 |
| 5,385,750 | 1/1995 | Aleksejczyk et al. | 427/4 |

FOREIGN PATENT DOCUMENTS 5-43403  2/1993  Japan.

OTHER PUBLICATIONS

Partyka, et al., "The Adsorption Of Non–Ionic Surfactants On A Silica Gel", *Colloids and Surfaces*, 12 (1984) 255–270.

*Primary Examiner*—S. Mark Clardy
*Attorney, Agent, or Firm*—Wayne C. Jaeschke; John E. Drach; Henry E. Millson, Jr.

[57] ABSTRACT

Compositions containing biologically active materials are readily formulated with polyhydroxy fatty acid amides as dispersants and/or wetting agents. The resultant compositions are environmentally acceptable in that they are readily biodegradable and easily applied to an agricultural substrate.

24 Claims, No Drawings

AGRICULTURALLY ACTIVE COMPOSITION COMPRISING POLYHYDROXY ACID AMIDE ADJUVANT

BACKGROUND OF THE INVENTION

1. Field of the Invention

This invention deals with the forming of dispersions or emulsions and dry product application of various biologically active ingredients. More specifically, this invention relates to compositions containing biologically active materials and a polyhydroxy fatty acid amide and a method of treating agricultural substrates with such compositions.

2. Description of the Related Art

Insecticides, insect repellents, fungicides, bactericides, bacteriostats, herbicides, and plant growth regulators are normally formulated into various products for use on crops, for insect control, weed control and the like. In some cases, the products are formulated as a liquid or a semi-solid dispersion. Whether the method of application is dry or wet, dispersing agents are normally incorporated into such compositions to control the flow of the product to ensure equal distribution of the active ingredient through the remaining components of the composition.

The typical composition used for fungicide, insecticide, bactericide or herbicide ingredients has ordinarily depended on the end-use method of application. That is, a specific dispersing aid is often employed when the product is to be applied in a powder or dry form and yet a second different dispersing aid is required when the product is to be applied as a semi-solid or liquid composition. It would be advantageous to prepare a product comprising the active ingredient and to utilize a single dispersing agent without regard to whether the final use application of the product is in a liquid or solid formulation. Moreover, the desirability of using a single ingredient as a dispersing agent reduces the possibility for error given the number of chemicals which must be compounded to prepare a herbicide or insecticide product.

It is also highly desirable to incorporate into the compositions with which the present invention deals, a dispersing aid which is not itself environmentally harmful either to the products to which it is applied or to the applicator of the composition. It is also desirable that the dispersing aid aspect of the present invention use a material which has emulsifying characteristics as well as being useful in dispersing the product in its application.

Polyhydroxy fatty acid amides are a class of nonionic surfactants which enjoy the advantage that they can be prepared using mainly renewable resources, such as fatty acid esters and sugars, and thereby provide substantial advantages to the formulators of surfactant-containing compositions who are seeking non-petrochemical, renewable resources for the manufacture of such compositions. Moreover, since the polyhydroxy fatty acid amides are readily biodegradable, they are ideally suited for use as dispersing agents and/or wetting agents in compositions containing biologically active materials such as agricultural chemical formulations.

SUMMARY OF THE INVENTION

It is an object of the present invention to use polyhydroxy fatty acid amides as dispersants, emulsifiers, and/or wetting agents in biologically active compositions such as agricultural chemical formulations which contain such biologically active materials as fungicides; bactericides, bacteriostats; insecticides; insect repellents; herbicides and/or plant growth regulators and mixtures thereof and inert carriers along with other adjuvants typically used in agricultural chemical formulations.

It has been discovered that compositions containing biologically active materials can be readily formulated with polyhydroxy fatty acid amides as dispersants and/or wetting agents. The resultant compositions are environmentally acceptable in that they are readily biodegradable and easily applied to an agricultural substrate.

Another aspect of the present invention is a method of treating an agricultural substrate which comprises introducing to the substrate a sufficient amount of a composition which is comprised of a biologically active material which includes an insecticide, insect repellent, fungicide, a bactericide, bacteriostat, herbicide, a plant growth regulator and the like and a polyhydroxy fatty acid amide. The composition can also contain an inert carrier and other adjuvants typically used in agricultural chemical formulations.

DETAILED DESCRIPTION OF THE INVENTION

Other than in the claims and in the operating examples, or where otherwise indicated, all numbers expressing quantities of ingredients or reaction conditions used herein are to be understood as modified in all instances by the term "about".

The term agricultural substrate as used herein means a plant, a plant pest, or a combination of a plant and a plant pest. A plant pest is defined as any living stage of any insects, mites, nematodes, slugs, snails, protozoa, or other invertebrate animals, bacteria, fungi, other parasitic plants or reproductive parts thereof, viruses, or any organisms similar to or allied with any of the foregoing, or any infectious substances which can directly or indirectly injure or cause disease or damage in any plants or parts thereof, or any processed, manufactured, or other products of plants.

The polyhydroxy fatty acid amides which can be used in the compositions and processes according to the invention are compounds of the formula I

wherein: $R_1$ is H, $C_1$–$C_4$, hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R_2$ is a $C_5$–$C_{31}$ hydrocarbyl moiety, preferably straight chain $C_7$–$C_{19}$ alkyl or alkenyl, more preferably straight chain $C_9$–$C_{17}$ alkyl or alkenyl, most preferably straight chain $C_{11}$–$C_{19}$ alkyl or alkenyl, or mixture thereof; and Y is a polyhydroxyhydrocarbyl moiety having a linear hydrocarbyl chain with at least 3 hydroxyls directly connected to the chain, or an alkoxylated derivative (preferably ethoxylated or propoxylated) thereof. Y preferably will be derived from a reducing sugar in a reductive amination reaction; more preferably Y is a glycityl moiety. Suitable reducing sugars include glucose, fructose, realrose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Y. It should be understood that it is by no means intended to exclude other suitable raw materials. Y preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, where n is an integer from 3 to 5, inclusive, and R' is H or a cyclic mono- or poly- saccharide, and alkoxylated derivatives thereof. Most preferred are glycityls wherein n is 4, particularly —$CH_2$—$(CHOH)_4$—$CH_2OH$. Compounds of the formula I are also known as glucamides. Therefore, when, for example, $R_1$ is methyl, $R_2$ dodecyl; and Y is —$CH_2$—$(CHOH)_4$—$CH_2OH$, the compound in question is referred to as dodecyl N-methylglucamide.

Methods for making polyhydroxy fatty acid amides are known in the art. In general, polyhydroxy fatty acid amides can be made by reductively aminating a reducing sugar reacting with an alkyl amine to form a corresponding N-alkyl polyhydroxyamine and then reacting the N-alkyl polyhydroxyamine with a fatty aliphatic ester or triglyceride to form the N-alkyl, polyhydroxy fatty acid amide. Processes for making polyhydroxy fatty acid amides are disclosed in U.S. Pat. Nos. 1,985,424; 2,965,576; 5,194,639; and 5,334,764 the entire contents of each of which is incorporated herein by reference.

The biologically active materials which can be used to make compositions according to the invention include, but are not limited to insecticides such as O,O-diethyl O-(2-isopropyl-4-methyl-6-pyrimidinyl)phosphorothioate, O,O-diethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethylS-(N-methyl-N-formylcarbamoylmethyl)phosphorodithioate, O,O-dimethyl S-2-[(ethylthio)ethyl]phosphorodithioate, O,O-diethyl S-2-[(ethylthio)ethyl]phosphorodithioate, O,O-dimethyl-1-hydroxy-2,2,2-trichloroethylphosphonate, O,O-diethyl-O-(5-phenyl-3-isooxazolyl)phosphorothioate, O,O-dimethyl O-(2,5-dichloro-4-bromophenyl)phosphorothioate, O,O-dimethyl-O-)3-methyl-4-methylmercaptophenyl)thiophosphate, O-ethyl O-p-cyanophenyl-O-phenylphosphorothioate, O,O-dimethyl-S-(1,2-dicarboethoxyethyl)phosphorodithioate, 2-chloro-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl)methyl]O,O-diethyl phosphorodithioate, 2-chloro-1-(2,4-dichlorophenyl)vinyl diethylphosphate O,O-diethyl O-(3-oxo-2-phenyl-2H-pyridazine-6-yl)phosphorothioate, O,O-dimethyl S-(1-methyl-2-ethylsulfinyl)-ethyl phosphorothiolate, O,O-dimethyl S-phthalimidomethyl phosphorodithioate, O,O-diethyl 2,2,2-trichloroethanol, 2-(p-tert-butyl-phenoxy)isopropyl-2'-chloroethylsulfite, azoxybenzene, di-(p-chlorophenyl)-cyclopropyl carbinol, di[tri(2,2-dimethyl-2-phenylethyl )tin ]oxide, 1-(4-chlorophenyl)-3-(2,6-difluorobenzoyl)urea and S-tricyclohexyltin O,O-diisopropylphosphorodithioate; 2-methyl-2-(methylthio)propionaldehyde O-(methylcarbamoyl ) oxime; ethyl [2-(4-phenoxyphenoxy)ethyl]carbamate; butyl-2,3-dihydro-2,2-dimethylbenzofuran-7-yl N,N'-dimethyl-N, N'thiodicarbarnate; 1-naphthyl methyl carbamate; 2-(ethylthiomethyl)phenyl methylcarbamate; 5-(4-phenoxybutyl)dimethylthiocarbamate; dimethyl N,N'-(thiobis(methylimino)carbonyloxy)-bis(ethanimidothioate); (RS)-α-cyano-3-phenoxybenzyl-(RS)-2-(4-chlorophenyl)-3-methylbutyrate; (RS)-α-ciano-3-phenoxyphenyl-(RS)-2,2-dichloro-1-(4-ethoxyphenyl) cyclopropanecarboxylate; (RS)-α-cyano-3-phenoxybenzyl-N-(2-chloro-α,α,α-trifluoro-p-tolyl-D-valinate; 3-phenoxybenzyl-(1RS)-cis,trans-3-(2,2-dichlorovinyl)- 2,2-diemthylcyclopropanedicarboxylate.

Insect repellents which may also be employed include but are not limited to 2-ethyl-1,3-hexanediol; N-octyl bicycloheptene dicarboximide; N,N-diethyl-M-toluamide; 2,3:4,5-Bis (2-butylene) tetrahydro-2-furaldehyde; Di-n-propyl isocinchomeronate; and 2-hydroxyethyl-n-octyl sulfide.

Fungicides which may also be employed include but are not limited to 3,3'-ethylenebis (tetrahydro-4,6-dimethyl-2H-1,3,5-thiadiazine-2-thione), zinc or manganese ethylenebis-(dithiocarbamate), bis-(dimethyldithiocarbamoyl)disulfide, zinc propylenebis (dithiocarbamate), bis(dimethyldithiocarbamoyl) ethylenediamine; nickel dimethyldithiocarbamate, methyl- 1(butylcarbamoyl)-2-benzimidazolecarbamate, 1,2-bis(3-mcthoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10,11-dehydrodibenzo (b,f)azepine; pyridine fungicides such as zinc bis(1-hydroxy-2(1H)pyridinethionate and 2-pyridinethiol-1-oxide sodium salt; O,O-diisopropyl S-benzylphosphorothioate and O-ethyl S,S-diphenyldithiophosphate; phthalimide fungicides such as N-(2,6-p-diethylphenyl)phthalimide and N-(2, 6-diethylphenyl)-4-methylphthalimide; dicarboxyimide fungicides such as N-trichloromethylthio 4-cyclohexene-1, 2-dicarboxyimide and N-tetrachloroethylthio-4-cyclohexene-1,2-dicarboxyimide; 5,6-dihydro-2-methyl-1,4-oxathine-3-carboxanilido-4,4-dioxide and 5,6-dihydro-2-methyl-1,4-oxathine-3-carboxanilide; naphthoquinone fungicides such as 2,3-dichloro-1,4-naphthoquinone, 2-oxy-3-chloro- 1,4-naphthoquinone copper sulfate, pentachloronitrobenzene; 1,4-dichloro-2,5-dimethoxybenzene; 5-methyl-s-triazol-(3,4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl- 1,2,4-thiazazole; 2,4-dichloro-6-(O-chloroanilino)-1,3,5-triazine; 2,3-dicyano-1, 4-dithioanthraquinone; copper 8-quinolinate; polyoxine; validamycin; cycloheximide; iron methanearsonate; diisopropyl 1,3-dithiolane-2-iridene malonate; 3-allyloxy-1,2-benzoisothiazol- 1,1-dioxide; kasugamycin; Blasticidin S; 4,5,6,7-tetrachlorophthalide; 3-(3,5-diclhlorophenyl)5-ethenyl5-methyloxazolizine-2,4-dione; N-(3,5-dichlorophenyl)-1,2-dimethylcyclopropane-1,2-dicarboxyimide; S-n-butyl-5'-para-t-butylbenzoic-N-3-pyridyldithiocarbonylimidate; 4-chlorophenoxy-3,3-dimethyl-1-(1H, 1,3,4-triazol-1-yl)-2-butanone;, methyl-D,L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinamide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolyl-[3,2,1 -i,j] quinoline-2-one; 3'-isopropoxy-2-methylbenzanilide; 1-[2-(2,4-dichlorophenyl)-4-ethyl-1,3-dioxorane-2-ylmethyl]-1H,1,2,4-triazol; 1,2-benzisolhiazoline-3-one; basic copper chloride; basic copper sulfate; N'-dichlorofluoromethylthio-N,N-dimethyl-N-phenyl sulfamide; ethyl-N-(3-dimethylaminopropyl)thiocarbamate hydrochloride; piomycin; S,S-6-methylquinoxaline-2,3-di-yldithiocarbonate; complex of zinc and manner; di-zinc bis(dimethyldithiocarbamate-)ethylenebis (dithiocarbamate).

Plant growth regulators which may also be employed include but are not limited to N-methoxycarbonyl-N'-4-methylcarbamoylethylisourea and 1-(4-chlorophenylcarbamoyl)-3-ethoxycarbonyl-2-methylisourea; another type of plant growth regulators such as sodium naphthaleneacetate, 1,2-dihydropyridazine-3,6-dione and gibberellins; traizine herbicides such as 2-methylthio-4,6-bisethylamino-1,3,5-triazine, 2-chloro-4,6-bisethylamino- 1,3,5-triazine, 2-methoxy-4-ethylamino-6-isopropylamino-1,3,5-triazine, 2-chloro-4-ethylamino-6-isopropylamino-s-triazine, 2-methylthio-4,6-bis(isopropylamino)-S-triazine and 2-methylthio-4-ethylamino-6-isopropylamino-s-triazine; phenoxy herbicides such as 2,4-dichlorophenoxyacetic acid and methyl, ethyl, and butyl esters thereof. 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether,2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl)carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiolcarbamate herbicides such as S-(4-chlorobenzyl)-N,N-diethylthiolcarbamate,S-ethyl-N-cyclohexyl-N-ethylthiolcarbamate and S-ethyl-hexahydro-1H-azepine-1-carbothioate and S-ethyl-N,N-di-n-propyl-thiocarbamate; pyridinium herbicides such as 1,1'-dimethyl-4,4'-bispyridinium dichloride; phosphoric herbicides such as N-(phosphonomethyl)glycine; aniline herbicides such as alpha, alpha, alpha-trifluoro-2,6-dinitro-N,N-dipropyl-p-toluidine, 4-(methylsulfonyl)-2,6-dinitro-N,N-dipropylaniline and N[3], N[3]-diethyl-2,4-dinitro--6trifluoromethyl-1,3-phenylene diamine; acid anilide herbicides such as 2-chloro-2',6'-diethyl-N-(butoxymethyl)acetoanilide, 2-chloro-2',6'-diethyl-N-(methoxymethyl)acetoanilide, and 3,4-dichloropropioneanilide; pyrazole herbicides such as 1,3-dimethyl-4-(2,4-dichlorobenzoyl )-5-hydroxypyrazole and 1,3-di-methyl-4-(2,4-dichlorobenzoyl)-5-(p-toluenesulfonyloxy)pyrazole; 5-tert-butyl-3-(2,4-dichloro-5-isopropoxyphenyl)- 1,3,4-oxadiazoline-2-one; 2-[N-isopropyl,N-(4-chlorophenyl)carbamoyl]-4-chloro-5-methyl-4-isooxazoline- 3-one; 3-isopropylbenzo-2-thia-1,3-diazinone-(4)-2,4-dioxide and 3-(2-methylphenoxy)pyridazine. The compositions according to the invention may also contain, for example, adjuvants such as powders, bulking agents, dyes, additional surfactants and solvents where required.

Other surfactants may be used in combination with the polyhydroxy fatty acid amides in the compositions according to the invention. Such surfactants are the well known nonionic, anionic, cationic and amphoteric surfactants. Especially preferred nonionic surfactants which can be used in combination with the polyhydroxy fatty acid amides in the compositions and processes according to the invention are alkyl polyglycosides of the formula II

    II wherein $R_3$ is monovalent organic radical having from about 6 to about 30 carbon atoms; $R_4$ is divalent elkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the compositions according to the invention have the formula I wherein Z is e glucose residue end b is zero. Such alkyl polyglycosides ere commercially available, for example, as APG®, GLUCOPON®, AGRIMUL®, or PLANTAREN® Surfectents from Henkel Corporation, Ambler, Pa., 19002. Examples of such surfectents include but are not limited to:

1. AGRIMUL® 2087 Surfactant—an alkyl polyglycoside in which the elkyl group contains 8 to 10 carbon atoms and having an average degree of polymerization of 1.7.
2. APG® 425 Surfactant—an elkyl polyglycoside in which the elkyl group contains 8 to 16 carbon atoms end having en average degree of polymerization of 1.6
3. APG® 625 Surfactant—an elkyl polyglycoside in which the elkyl groups contains 12 to 1 carbon atoms end having en average degree of polymerization of 1.6.
4. AGRIMUL® 2069 Surfactant—an alkyl polyglycoside in which the alkyl groups contains 9 to 11 carbon atoms and having an average degree of polymerization of 1.6.
5. GLUCOPON® 600 Surfactant—an alkyl polyglycoside in which the alkyl groups contains 12 to 16 carbon atoms and having an average degree of polymerization of 1.4.
6. PLANTAREN® 2000 Surfactant—a $C_{8-6}$ alkyl polyglycoside in which the alkyl group contains 8 to 16 carbon atoms and having an average degree of polymerization of 1.4.
7. PLANTAREN® 1300 Surfactant—a (12–16 alkyl polyglycoside in which the alkyl groups contains 12 to 16 carbon atoms and having an average degree of polymerization of 1.6.

Other examples include alkyl polyglycoside surfactant compositions which are comprised of mixtures of compounds of formula II wherein Z represents a moiety derived from a reducing saccharide containing 5 or 6 carbon atoms; a is a number having a value from 1 to about 6; b is zero; and $R_3$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference. The amount of other surfactants such as the alkyl polyglycosides of formula II which can be used can range from about 1% to about 99% based on the total amount of surfactant and will preferably be from about 10% to about 90%.

The compositions according to the invention can also contain a solid phase surfactant which is comprised of a combination of an alkyl polyglycoside and an inert carrier in addition to the polyhydroxy fatty acid amides as set forth herein. The alkyl polyglycosides which can be used are compounds of the formula II as set forth above. Such compositions, which assume a dry form and can easily undergo dry blending and milling, and are generally comprised of (1) a biologically active ingredient selected from the group consisting of a fungicide; a bactericide, a bacteriostat; an insecticide; an insect repellent; an herbicide; a plant growth regulator and mixtures thereof and, (2) a compound of the formula I

wherein: $R_1$ is H, $C_1$–$C_4$ hydrocarbyl, 2-hydroxy ethyl, 2-hydroxy propyl, or a mixture thereof, and $R_2$ is a $C_5$–$C_{31}$ hydrocarbyl moiety, and Y is a polyhydroxyhydrocarbyl moiety having a linear hydrocarbyl chain with at least 3 hydroxyls directly connected to the chain, or an alkoxylated derivative thereof; (3) a solid surfactant comprised of: (a) a compound of the formula II

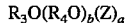

wherein $R_3$ is a monovalent organic radical having from about 6 to about 30 carbon atoms; $R_4$ is divalent alkylene radical having from 2 to 4 carbon atoms; Z is a saccharide residue having 5 or 6 carbon atoms; b is a number having a value from 0 to about 12; a is a number having a value from 1 to about 6; and (b) and an inert carrier selected from the group consisting of silica, talc, a zeolite, magnesium aluminum silicate, calcium sulfate, magnesium carbonate, magnesium oxide, aluminum oxide. Preferably, the inert carrier is silica. It is also preferred that the weight ratio of the compound of formula I to the inert carrier is from about 0.10 to about 0.90 and more preferably from about 0.40 to about 0.80 and most preferably from about 0.60 to about 0.65. Preferred compounds of formula II are those wherein b is zero; $R_3$ is a monovalent organic radical having from about 6 to about 30 carbon atoms; Z is a saccharide residue having 5 or 6 carbon atoms; a is a number having a value from 1 to about 6. Most preferably, compounds of formula II are those wherein $R_3$ is a monovalent organic radical having from about 8 to about 10 carbon atoms; Z is a glucose residue; and a is about 1.7 and those wherein $R_3$ is a monovalent organic radical having from about 9 to about 11 carbon atoms; Z is a glucose residue; and a is about 1.6. Compositions containing polyhydroxy fatty acid amides wherein $R_1$ is $CH_3$; $R_2$ is $C_{11}H_{23}$ group; and Y is —$CH_2$—(CHOH)$_2$(CHOR')(CHOH)—$CH_2OH$ are preferred. Compositions containing polyhydroxy fatty acid amides wherein $R_1$ is $CH_3$; $R_2$ is a mixture of $C_{15}H_{31}$ and $C_{17}H_{34}$; and Y is —$CH_2$—(CHOH')$_2$(CHOR')(CHOH)—$CH_2OH$ are also preferred. Similar compositions are disclosed in copending application Ser. No. 08/227,934, filed on Apr. 15, 1994, the entire contents of which are incorporated herein by reference.

The amount of solid phase surfactants which can be used can range from about 1% to about 10% based on the total amount of surfactant and will preferably be from about 2% to about 10%.

The biologically active ingredients in the present invention can be present in a formulation in an amount up to about 95% of the total formulation weight. Typically, biologically active ingredients are formulated so as to be present in a composition at from about 0.0001 percent to about 10 percent by weight; preferably from about 0.0005 percent to about 8 percent by weight. The end usage level of the products is therefore dependent upon the amount of the compositions of the present invention. It is thus within the skill of the applicator to determine the specific amount of active ingredient to be used in any particular application.

The compositions of the present invention can be formulated with or without solvents such as water and other solvents typically used in formulations containing biologically active ingredients. Since the polyhydroxy fatty acid amides the present invention can be utilized as solids, formulations containing biologically active ingredients can be made which contain all solid components. On the other hand, since other types of formulations can contain liquid surfactants, it is possible that some formulations containing biologically active ingredients and the polyhydroxy fatty acid amides the present invention can be neat liquids. It is also possible that formulations containing biologically active ingredients and the polyhydroxy fatty acid amides the present invention can contain water. In such instances, typical formulations will contain from about 5 percent to about 95 percent; preferably from about 10 percent to about 95 percent by weight water. Additional solvents may be added by the applicator to dilute out the composition. Of course, the products of the present invention may be formulated as aqueous products ready for use if desired. The products may be applied by aerial spraying, by in seed row application or with a fertilizer or the like.

It is anticipated that the biologically active materials disclosed herein will be utilized in their normal use level or slightly lower levels due to the enhanced effectiveness of the compositions of the present invention. The polyhydroxy fatty acid amides the present invention will be utilized in the composition typically at from about 0.1 percent to about 20 percent; preferably from about 0.5 percent to about 10 percent by weight of the composition. It is thus within the skill of the applicator to determine the specific amount of adjuvants such as powders, bulking agents dyes, additional surfactants and solvents in the compositions of the present invention.

The following are suggested exemplifications of the present invention but are not meant to limit the invention to the recited examples.

EXAMPLE 1

About 20 parts of 5-bromo-3-sec-butyl-6-methyluracil, 5 parts of dodecyl N-methylglucamide, 3 parts of calcium lignosulfonate and 72 parts of diatomaceous earth are mixed together and ground uniformly to give a wettable powder containing 20 percent by weight of the active ingredient compound.

EXAMPLE 2

About 30 parts of 2,2-dichlorovinyl dimethyl phosphate, 50 parts of xylene and 20 parts of cetylstearyl N-methylglucamide are mixed together to make a uniform solution, affording an emulsifiable concentrate containing 30 percent by weight of the active ingredient compound.

EXAMPLE 3

About 50 parts of 3-methyl-4-chlorobenzthiazol-2-one and 50 parts of N-methyl, dodecylglucamide are mixed together to make a uniform mixture, affording an oily formulation containing 50 percent by weight of the active ingredient compound.

EXAMPLE 4

About 40 parts of finely divided N-methoxycarbonyl-N'-4-methylcarbamoylethylisourea having average particle size of not more than 10 microns, 4 parts of dodecyl N-methylglucamide, 1 part of hydroxypropylcellulose and 55 parts of water are mixed together uniformly to give a sol containing 40 percent by weight of the active ingredient compound.

EXAMPLE 5

An insect repellent is prepared containing 1 part N,N-Diethyl-M-toluamide; 5 parts dodecyltetradecyl N-methylglucamide; and 94 parts octyl alcohol.

EXAMPLE 6

A mixture of the following components should result in a wettable powder formulation according to the invention. A wettable powder composition containing Chlorothalonil can be prepared having the following composition:

| Component | Wt. % |
| --- | --- |
| Chlorothalonil (95%) | 78.94 |
| Dodecyltetradecyl N-methylglucamide | 3.00 |
| Lomar ® PW | 2.00 |
| Foamaster Soap L | 0.50 |
| Barden Clay | 15.56 |

EXAMPLE 7

A mixture of the following components should result in a water dispersible granule composition according to the invention. A water dispersible granule composition containing Atrazine can be prepared having the following composition:

| Component | Wt. % |
| --- | --- |
| Atrazine (98%) | 91.83 |
| Dodecyltetradecyl N-methylglucamide | 2.75 |
| Lomar ® PW | 5.0 |
| Foamaster Soap L | 0.25 |
| HiSil 233 | 0.17 |

EXAMPLE 8

A mixture of the following components should result in a water dispersible granule composition according to the invention. A water dispersible granule composition containing Fluometuron can be prepared having the following composition:

| Component | Wt. % |
| --- | --- |
| Tech. Fluometuron(97%) | 88.7 |
| Dodecyl N-methylglucamide | 3.0 |
| Lomar ® PW | 3.0 |
| HiSil 233 | 5.3 |

EXAMPLE 9

A mixture of the following components should result in an emulsifiable concentrate composition according to the invention. An emulsifiable concentrate composition containing Chlorpyrifos can be prepared having the following composition:

| Component | Wt. % |
| --- | --- |
| Technical Chlorpyrifos(95%) | 42.8 |
| Aromatic Solvent 150 | 52.2 |

-continued

| Component | Wt. % |
| --- | --- |
| Trylox 5909 POE(40)Castor Oil | 1.0 |
| Calcium DDBSA | 2.0 |
| Cetylstearyl N-methylglucamide | 2.0 |

EXAMPLE 10

A mixture of the following components should result in a concentrated emulsion composition according to the invention. A concentrated emulsion composition containing permethrin can be prepared having the following composition:

| Component | Wt. % |
| --- | --- |
| Technical Permethrin 96% | 25.0 |
| Aromatic Solvent 150 | 20.0 |
| Tryfac 5556 Phosphate Ester | 2.0 |
| Agrimul PG ® 2069 | 0.5 |
| Cetylstearyl N-methylglucamide | 2.0 |
| Dipropylene Glycol | 4.0 |
| Water | 46.5 |

EXAMPLE 11

About 20 parts of 5-bromo-3-sec-butyl-6-methyluracil, 2.5 parts of dodecyl N-methylglucamide, 2.5 parts of Agrimul PG® 2069,3 parts of calcium lignosulfonate and 72 parts of diatomaceous earth are mixed together and ground uniformly to give a wettable powder containing 20 percent by weight of the active ingredient compound.

EXAMPLE 12

About 30 parts of 2,2-dichlorovinyl dimethyl phosphate, 50 pads of xylene and 10 parts of cetylstearyl N-methylglucamide, and 10 parts of AGRIMUL® 2067 are mixed together to make a uniform solution, affording an emulsifiable concentrate containing 30 percent by weight of the active ingredient compound.

What is claimed is:

1. A composition for treating an agricultural substrate comprising: (1) a compound of the formula I

wherein: $R_1$ is H, $C_1$–$C_4$ hydrocarbyl, 2-hydroxy ethyl, 2-hydroxy propyl, or a mixture thereof, and $R_2$ is a $C_5$–$C_{31}$ hydrocarbyl moiety, and Y is a polyhydroxyhydrocarbyl moiety having a linear hydrocarbyl chain with at least 3 hydroxyls directly connected to the chain, or an alkoxylated derivative thereof and; (2) a biologically active ingredient selected from the group consisting of a fungicide; an insecticide; an insect repellent; an herbicide; a plant growth regulator and mixtures thereof.

2. The composition of claim 1 wherein said biologically active ingredient is an herbicide.

3. The composition of claim 1 wherein $R_1$ is a $C_1$–$C_4$ alkyl group.

4. The composition of claim 3 wherein $R_1$ is a methyl group.

5. The composition of claim 1 wherein $R_2$ is a straight chain $C_7$–$C_{19}$ alkyl or alkenyl group.

6. The composition of claim 1 wherein Y is a glyceryl moiety.

7. The composition of claim 1 wherein Y is —CH$_2$—(CHOH)$_2$(CHOR')(CHOH)—CH$_2$OH.

8. The composition of claim 1 wherein R$_1$ is CH$_3$; R$_2$ is C$_{11}$H$_{23}$ group; and Y is —CH$_2$—(CHOH)$_2$(CHOR')(CHOH)—CH$_2$OH.

9. The composition of claim 1 wherein R$_1$ is CH$_3$; R$_2$ is a mixture of C$_{15}$H$_{31}$ and C$_{17}$H$_{34}$; and Y is —CH$_2$—(CHOH)$_2$(CHOR')(CHOH)—CH$_2$OH.

10. The composition of claim 1 further comprising a compound of the formula II $$R_3O(R_4O)_b(Z)_a \qquad \text{II}$$

wherein R$_3$ is a monovalent organic radical having from about 6 to about 30 carbon atoms; R$_4$ is divalent alkylene radical having from 2 to 4 carbon atoms; Z is a saccharide residue having 5 or 6 carbon atoms; b is a number having a value from 0 to about 12; a is a number having a value from 1 to about 6.

11. The composition of claim 10 wherein b is zero; R$_3$ is a monovalent organic radical having from about 6 to about 30 carbon atoms; Z is a saccharide residue having 5 or 6 carbon atoms; a is a number having a value from 1 to about 6.

12. The composition of claim 11 wherein alkyl group R$_3$ is a monovalent organic radical having from about 8 to about 10 carbon atoms; Z is a glucose residue; and a is about 1.7.

13. The composition of claim 11 wherein alkyl group R$_3$ is a monovalent organic radical having from about 9 to about 11 carbon atoms; Z is a glucose residue; and a is about 1.6.

14. A composition for treating an agricultural substrate comprising: (1) a biologically active ingredient selected from the group consisting of a fungicide; an insecticide; an insect repellent; an herbicide; a plant growth regulator and mixtures thereof and, (2) a compound of the formula I $$\underset{R_2-C-N-Y}{\overset{\overset{O}{\|} \quad \overset{R_1}{|}}{}} \qquad (I)$$

wherein: R$_1$ is H, C$_1$–C$_4$ hydrocarbyl, 2-hydroxy ethyl, 2-hydroxy propyl, or a mixture thereof, and R$_2$ is a C$_5$–C$_{31}$ hydrocarbyl moiety, and Y is a polyhydroxyhydrocarbyl moiety having a linear hydrocarbyl chain with at least 3 hydroxyls directly connected to the chain, or an alkoxylated derivative thereof; (3) a solid surfactant comprised of: (a) a compound of the formula II $$R_3O(R_4O)_b(Z)_a \qquad \text{II}$$

wherein R$_3$ is a monovalent organic radical having from about 6 to about 30 carbon atoms; R$_4$ is divalent alkylene radical having from 2 to 4 carbon atoms; Z is a saccharide residue having 5 or 6 carbon atoms; b is a number having a value from 0 to about 12; a is a number having a value from 1 to about 6; and (b) and an inert carrier selected from the group consisting of silica, talc, a zeolite, magnesian aluminum silicate, calcium sulfate, magnesium carbonate, magnesium oxide, aluminum oxide.

15. The composition of claim 14 wherein the weight ratio of said compound of formula I to said inert carried is from about 0.10 to about 0.90.

16. The composition of claim 15 wherein said weight ratio is from about 0.40 to about 0.80.

17. The composition of claim 16 wherein said weight ratio is from about 0.60 to about 0.65.

18. The composition of claim 14 wherein in said compound of the formula II R$_3$ is an alkyl group having from 8 to 10 carbon atoms; b is zero; Z is a glucose residue; and a is about 1.7.

19. The composition of claim 14 wherein in said compound of the formula II R$_3$ is an alkyl group having from 9 to 11 carbon atoms; b is zero; Z is a glucose residue; and a is about 1.6.

20. The composition of claim 14 wherein said inert carrier is silica.

21. The composition of claim 14 wherein R$_1$ is CH$_3$; R$_2$ is CH$_{11}$H$_{23}$ group; and Y is —CH$_2$—(CHOH)$_2$(CHOR')(CHOH)—CH$_2$OH.

22. The composition of claim 14 wherein R$_1$ is CH$_3$; R$_2$ is a mixture of C$_{15}$H$_{31}$ and C$_{17}$H$_{34}$; and Y is —CH$_2$—(CHOH)$_2$(CHOR')(CHOH)—CH$_2$OH.

23. A method for treating an agricultural substrate comprising contacting said substrate with a treatment effective quantity of a composition comprising: (1) a compound of the formula I $$\underset{R_2-C-N-Y}{\overset{\overset{O}{\|} \quad \overset{R_1}{|}}{}} \qquad (I)$$

wherein: R$_1$ is H, C$_1$–C$_4$ hydrocarbyl, 2-hydroxy ethyl, 2-hydroxy propyl, or a mixture thereof, and R$_2$ is a C$_5$–C$_{31}$ hydrocarbyl moiety, and Y is a polyhydroxyhydrocarbyl moiety having a linear hydrocarbyl chain with at least 3 hydroxyls directly connected to the chain, or an alkoxylated derivative thereof and; (2) a biologically active ingredient selected from the group consisting of a fungicide; a bactericide, a bacteriostat; an insecticide; an insect repellent; an herbicide; a plant growth regulator and mixtures thereof.

24. A method for treating an agricultural substrate comprising contacting said substrate with a treatment effective quantity of a composition comprising: (1) a biologically active ingredient selected from the group consisting of a fungicide; a bactericide, a bacteriostat; an insecticide; an insect repellent; an herbicide; a plant growth regulator and mixtures thereof, (2) a compound of the formula I $$\underset{R_2-C-N-Y}{\overset{\overset{O}{\|} \quad \overset{R_1}{|}}{}} \qquad (I)$$

wherein: R$_1$ is H, C$_1$–C$_4$ hydrocarbyl, 2-hydroxy ethyl, 2-hydroxy propyl, or a mixture thereof, and R$_2$ is a C$_5$–C$_{31}$ hydrocarbyl moiety, end Y is a polyhydroxyhydrocarbyl moiety having a linear hydrocarbyl chain with at least 3 hydroxyls directly connected to the chain, or an alkoxylated derivative thereof; and (3) a solid surfactant comprised of:

(a) a compound of the formula II $$R_3O(R_4O)_b(Z)_a \qquad \text{II}$$

wherein R$_3$ is a monovalent organic radical having from about 6 to about 30 carbon atoms; R$_4$ is divalent alkylene radical having from 2 to 4 carbon atoms; Z is a saccharide residue having 5 or 6 carbon atoms; b is a number having a value from 0 to about 12; a is a number having a value from 1 to about 6; and (b) and an inert carrier selected from the group consisting of silica, talc, a zeolite, magnesium aluminum silicate, calcium sulfate, magnesium carbonate, magnesium oxide, aluminum oxide.

* * * * *